Dec. 8, 1959 H. C. SWIM Plant Pat. 1,884
PEACH TREE
Filed Nov. 28, 1958
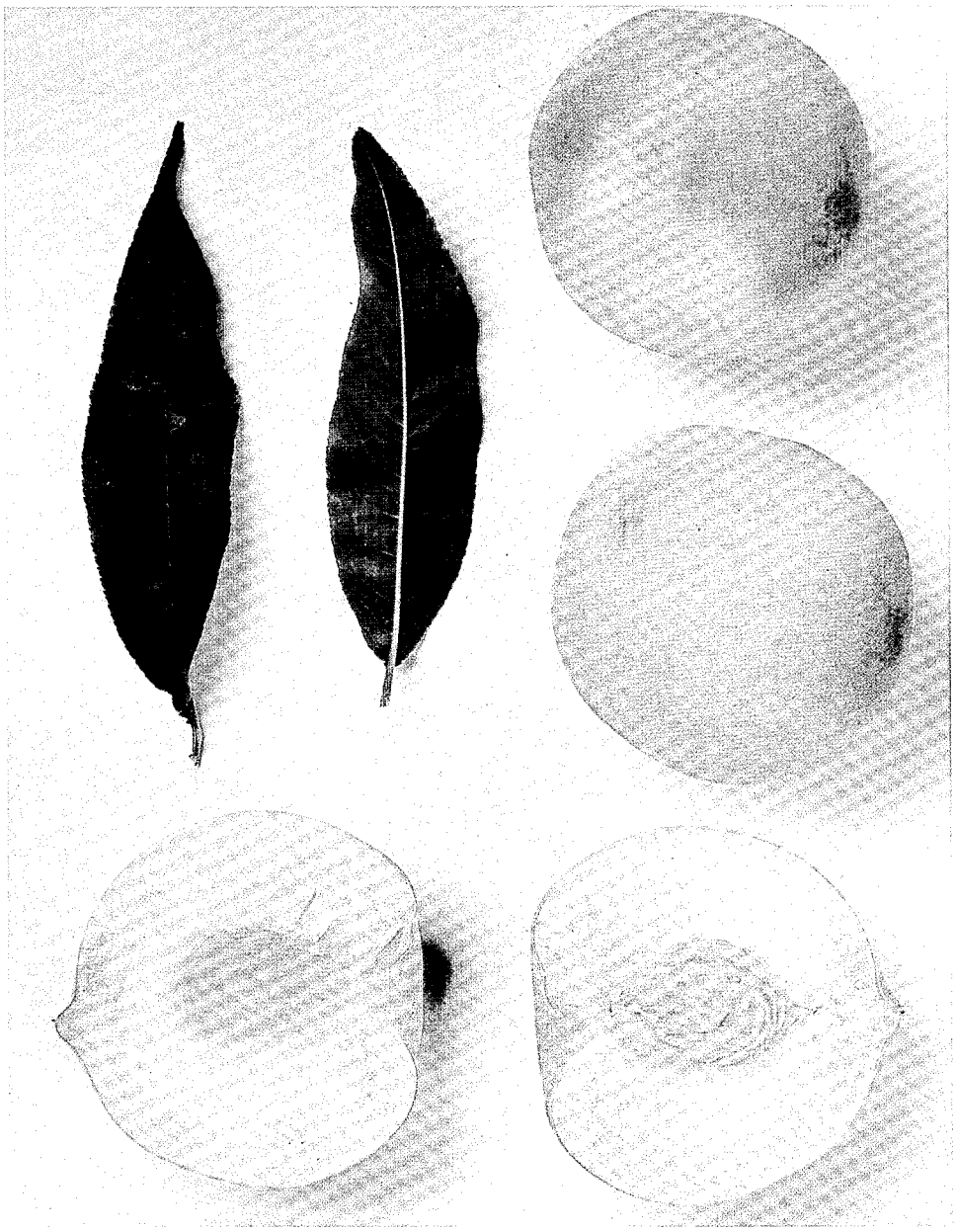
Inventor
H. C. Swim
By: Robert Cobb
Attorneys United States Patent Office Plant Pat. 1,884
Patented Dec. 8, 1959

1,884

PEACH TREE

Herbert C. Swim, Ontario, Calif., assignor to Armstrong Nurseries, Inc., Ontario, Calif., a corporation of California Application November 28, 1958, Serial No. 777,162

1 Claim. (Cl. 47—62)

The present invention relates to a new and distinct variety of peach tree of the yellow-fleshed, freestone, fruit-bearing type, which was originated by me by crossing the variety "Flamingo" (Plant Patent No. 661) with the variety "Springtime" (Plant Patent No. 1,268).

The primary objective of this breeding was to produce a moderately early ripening yellow-fleshed, freestone peach variety which bears largef ruit with firm flesh and attractive skin color, combined with high eating quality and good flavor. This objective was fully achieved by combining the factors for earliness which are inherent in the pollen parent "Springtime," with the factors for large size, firmness and high quality which are inherent in the seed parent "Flamingo," together with the yellow-fleshed factor present in but not exhibited by "Springtime," and exhibited by "Flamingo," along with the characteristic high skin color and generally attractive appearance of the fruit of both parent varieties. As the result of this breeding, the new variety is particularly characterized as to novelty by the following unique combination of outstanding features which distinguish it from its parents as well as from all other varieties of which I am aware:

(1) A vigorous habit of growth, combined with a chilling requirement about equal to or slightly more than that of "Springtime";

(2) Very large yellow-fleshed freestone fruit of high quality;

(3) A fruit firmness sufficient for good shipping qualities;

(4) A good "peach" flavor of the fruit, with a delectable balance between sweetness and acidity;

(5) An attractive skin color of the fruit which is highly blushed and mottled with red; and (6) A mid-June ripening period of the fruit in southern California, with a maturation period from peak bloom to first fruit-ripening of one or two weeks longer than that of the variety "Robin" (Plant Patent No. 529).

In comparison with the seed parent, "Flamingo," the tree of the new variety is more vigorous in its habit of growth than the rather moderate growth of "Flamingo"; the new variety has a lower chilling requirement than this parent, and the fruit ripens about mid-June and hence much earlier than the usual ripening period of "Flamingo" which is late July or early August in southern California.

As compared with the pollen parent, "Springtime," the new variety is yellow-fleshed, whereas the fruit of "Springtime" is white-fleshed; the fruit is considerably larger; the flesh of the fruit is considerably more free from the pit; and the new variety ripens later, usually in mid-June, instead of from mid-May to early June, as in the case of "Springtime" in southern California.

Asexual reproduction of the new variety by grafting, as performed at Ontario, California, shows that the foregoing characteristics and distinctions come true to form and are established and transmitted through succeeding propagations.

The accompanying drawing shows typical specimens of the foliage and fruit of my new variety, with the upper and lower surfaces of the foliage being illustrated, and with both exterior and sectional views of the fruit being shown, all as depicted in color as nearly true as it is reasonably possible to make the same in a color illustration of this character.

The following is a detailed description of my new variety, as based upon observations of specimens grown at Ontario, California, with color terminology in accordance with Robert F. Wilson's Horticultural Colour Chart (hereinafter abbreviated as "Wilson") and Ridgway's Color Standards and Nomenclature (hereinafter abbreviated as "Ridgway"), except where general color terms of ordinary dictionary significance are obvious:

*Tree*

Habit: Vigorous; upright-spreading.
Fruit production: Very good; regular bearer.
Current growth:
- *Surface texture.*—Smooth at first, with lenticels small and minute. With age, larger, cracked, slightly raised lenticels appear toward base of the more vigorous shoots.
- *Color.*—Green or slightly reddish at first on exposed surfaces, with lenticels appearing as small, nearly white dots; all becoming brown with age.

2-year wood:
- *Surface texture.*—Generally smooth, with slightly raised, irregular, longitudinal striations and numerous lenticels.
- *Color.*—From greenish brown to brown.

Old wood:
- *Surface texture.*—Generally smooth, with moderate number of large, raised lenticels and occasional deep longitudinal fissures.
- *Color.*—From grey to greyish brown or reddish brown on more exposed surfaces.

Leaves:
- *Size.*—Length—from 5½ inches to 7 inches. Width—from 1½ inches to 2 inches.
- *Shape.*—Lanceolate, with apex acuminate.
- *Color.*—Upper surface—dark green. Lower surface—lighter green.
- *Petiole.*—Medium length.
- *Margin.*—Finely serrate; glandular.
- *Glands.*—Globose; from small to medium size; usually 2 but sometimes 4 in number; borne on the base of the blade.
- *Stipules.*—Short; broad at base; early deciduous.

Vegetative buds:
- *Shape.*—Ovoid, unless compressed between flower buds.
- *Scales.*—Pubescence thick and of moderate length.
- *Color.*—Dark brown.

*Flowers*

Dates of first and full bloom: Over prolonged period of observation, varied widely from February 8th to March 10th for first bloom, and from February 16th to March 25th for full bloom, due to weather variations from year-to-year.

Dormant flower buds:
- *Shape.*—Ovoid.
- *Scales.*—Thick pubescence of moderate length.
- *Color.*—Dark brown.

Size (when fully open): showy; medium size.
Petalage: Single; usually 5 petals.
Color (open flower): Near Neyron Rose, Plate 623/2, page 76 (Wilson).

*Fruit*

Ripening dates: Generally ripens in mid-June at Ontario,

California; length of fruit maturation period from peak bloom to first ripe is about 1 or 2 weeks longer than that of "Robin" peach; over prolonged period of observation, dates of first ripening ranged from June 2nd to June 24th.

Maturity when described: Eating ripe.

Size: Slightly variable, but generally large.

*Axial diameter.*—From 2½ inches to 2¾ inches.

*Transverse diameter in suture plane.*—From 2⅝ inches to 3 inches.

*Transverse diameter at right angles to suture plane.*—From 2½ inches to 2¾ inches.

Form: Somewhat variable; slightly asymmetrical; broadly ovoid; sometimes compressed laterally toward suture.

Suture: Usually a shallow line extending from base to apex, with slight depression beyond pistil point.

Ventral surface: Slightly lipped toward apex; lips unequal.

Stem cavity: Rounded; elongated in suture plane, with suture showing on one side.

*Depth.*—About ⅜ inch.

*Width.*—From about ⅝ inch to about ¾ inch.

Base: From rounded to truncate.

Apex: Generally short and only slightly prolonged in most seasons; pistil point short and apical.

Stem: Medium caliper; glabrous; medium adherence to stone. Length—about ½ inch.

Skin:

*Thickness.*—From medium to thin.

*Texture.*—Medium.

*Tenacity to flesh.*—Frees easily.

*Pubescence.*—Moderate; medium length.

*Color.*—Base color varies between Saffron Yellow, Plate 7/2, page 7 (Wilson) and Saffron Yellow, Plate 7/3, page 7 (Wilson), mottled, flecked and blushed with near Delft Rose, Plate 020/2, page 108 (Wilson), and near Carmine, Plate 21/1, page 21 (Wilson).

Flesh:

*Quality.*—Firm; melting; with fine, tender fibres.

*Aroma.*—Pronounced.

*Flavor.*—Good "peach" flavor, having a good balance between sugar and acid.

*Color.*—Between Lemon Yellow, Plate 4/2, page 4 (Wilson) and Indian Yellow, Plate 6/2, page 6 (Wilson), with streaks and flecks of near Geranium Lake, Plate 20/1, page 20 (Wilson) particularly near the apex and to a lesser extent toward the base; essentially no red coloring on the surface of the pit cavity.

Stone:

*Tenacity to flesh.*—Free; sometimes adheres somewhat to flesh along ventral edge.

*Size.*—Length—about 1¼ inches. Width—from about ⅞ inch to 1 inch. Thickness—from about ⅝ inch to about ¾ inch.

*Form.*—Obovate.

*Base.*—Somewhat oblique.

*Hilum.*—Oblong.

*Apex.*—Sharply acute.

*Sides.*—Slightly unequal; irregularly furrowed and pitted throughout; more ridged toward apex and pitted toward base.

*Ventral edge.*—Medium thickness; with wing generally throughout.

*Dorsal edge.*—Medium thickness; shallow, narrow groove toward base; ridges on either side interrupted.

*Color.*—Near Light Ochraceous-Buff, Plate XV (Ridgway).

I claim:

A new and distinct variety of peach tree of the yellow-fleshed, freestone, fruit-bearing type, substantially as herein shown and described, characterized particularly as to novelty by the unique combination of a vigorous habit of growth, a chilling requirement approximating that of the variety "Springtime" (Plant Patent No. 1,268), very large fruit having a firmness sufficient for good shipping qualities, said fruit having a good "peach" flavor and a balanced blend of sweetness and acidity, an attractive skin color which is highly blushed and mottled with red, and a mid-June ripening period in the geographical area of southern California, with a maturation period from peak bloom to first fruit ripening of 1 or 2 weeks longer than that of the variety "Robin" (Plant Patent No. 529).

No references cited.